(12) United States Patent
Miyoshi

(10) Patent No.: US 9,232,918 B2
(45) Date of Patent: Jan. 12, 2016

(54) IMAGE DISPLAY APPARATUS, DISPLAY CONTROL METHOD, AND DISPLAY CONTROL PROGRAM

(71) Applicant: Seiko Epson Corporation, Shinjuku-ku (JP)

(72) Inventor: Kazuhiro Miyoshi, Matsumoto (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 14/395,280

(22) PCT Filed: Apr. 10, 2013

(86) PCT No.: PCT/JP2013/002440
§ 371 (c)(1),
(2) Date: Oct. 17, 2014

(87) PCT Pub. No.: WO2013/157227
PCT Pub. Date: Oct. 24, 2013

(65) Prior Publication Data
US 2015/0071512 A1    Mar. 12, 2015

(30) Foreign Application Priority Data

Apr. 18, 2012    (JP) ................................ 2012-094525

(51) Int. Cl.
*G06K 9/00*    (2006.01)
*A61B 5/00*    (2006.01)
(Continued)

(52) U.S. Cl.
CPC ............. *A61B 5/4035* (2013.01); *A61B 5/0002* (2013.01); *A61B 5/0261* (2013.01); *A61B 5/681* (2013.01); *A61B 5/742* (2013.01)

(58) Field of Classification Search
USPC ......... 382/100, 103, 106–107, 128–134, 162, 382/165, 173, 181, 189, 209, 214, 232, 254, 382/274, 276, 286, 294, 305, 312; 378/4, 378/21; 600/27, 481, 424; 607/54; 463/36
See application file for complete search history.

(56) References Cited

U.S. PATENT DOCUMENTS

2002/0013533 A1\* 1/2002 Oka .................... A61B 5/14539
                                                            600/481
2008/0214903 A1   9/2008 Orbach
(Continued)

FOREIGN PATENT DOCUMENTS

JP    09-238908 A    9/1997
JP    10-071137 A    3/1998
(Continued)

*Primary Examiner* — Seyed Azarian
(74) *Attorney, Agent, or Firm* — Kilpatrick Townsend & Stockton LLP

(57) ABSTRACT

An image display apparatus includes a display section (display unit) that displays an image, an information acquisition section that acquires predominance levels of sympathetic nerves and parasympathetic nerves and an activity magnitude of the autonomic nerves based on the biological information, an image generation section that generates the biological state image in which a figure having a size according to the acquired activity magnitude of the autonomic nerves is set along a first axis, along one side of which the predominance level of the sympathetic nerves is set with respect to a reference point and along the other side of which the predominance level of the parasympathetic nerves is set with respect to the reference point, in a position according to the acquired predominance levels of the sympathetic nerves and the parasympathetic nerves.

5 Claims, 12 Drawing Sheets

(51) Int. Cl.
*A61B 5/026* (2006.01)
*A61B 5/02* (2006.01)

(56) References Cited

U.S. PATENT DOCUMENTS

| | | | |
|---|---|---|---|
| 2008/0214931 A1* | 9/2008 | Dickfeld | A61B 5/042 600/424 |
| 2009/0312817 A1* | 12/2009 | Hogle | A61B 5/0492 607/54 |
| 2010/0249494 A1* | 9/2010 | Yoshizawa | A61B 5/4035 600/27 |
| 2013/0231186 A1* | 9/2013 | Yoshizawa | A61B 5/4035 463/36 |

FOREIGN PATENT DOCUMENTS

| | | |
|---|---|---|
| JP | 2001-353131 A | 12/2001 |
| JP | 2005-192873 A | 7/2005 |
| JP | 2008-532587 A | 8/2008 |
| JP | 2008-217274 A | 9/2008 |
| WO | 2011/061865 A1 | 5/2011 |

* cited by examiner

IMAGE DISPLAY APPARATUS, DISPLAY CONTROL METHOD, AND DISPLAY CONTROL PROGRAM

This application is a U.S. National Phase Application of International Application No. PCT/JP2013/002440, filed Apr. 10, 2013, which claims priority to Japanese Patent Application No.: 2012-094525, filed Apr. 18, 2012, the entireties of which are all hereby incorporated by reference.

TECHNICAL FIELD

The present invention relates to an image display apparatus, a display control method, and a display control program for displaying an image showing the state of autonomic nerves.

BACKGROUND ART

There is a known notification system that notifies information on wakefulness of a subject operator (see PTL 1, for example).

The notification system described in PTL 1 is formed of a control center, a plurality of terminals, and a network that connects the control center and the plurality of terminals to each other. Among them, the control center receives information on the wakefulness and associated factors acquired from the subject operator via the corresponding terminal and creates processed information based on the information on the wakefulness and associated factors. The control center then transmits the processed information to the terminal that the subject operator is using, and the terminal notifies the subject operator of the processed information. The processed information is alternatively created by the corresponding terminal in some cases.

The information on the wakefulness and associated factors described above contains physiological information, such as an electrocardiographic waveform, the heart rate, the brain wave, and the pulse, and information on whether the subject operator is present. When the information on the wakefulness and associated factors is provided in the form of an electrocardiographic waveform, peaks at 0.1 Hz and therearound provide the action levels of the sympathetic nerves and the parasympathetic nerves, and peaks at 0.3 Hz and therearound provide the action level of the parasympathetic nerves.

Examples of the processed information described above include information in the form of graphs representing the resultant action levels and information representing the distribution of the wakefulness and the position of the subject operator in the distribution. Other examples of the processed information include information representing the information on the wakefulness and associated factors and a preferable range and information representing the average of wakefulness levels in a predetermined period (one day, for example) and the current wakefulness level.

CITATION LIST

Patent Literature

PTL 1: JP-A-2005-192873

SUMMARY OF INVENTION

Technical Problem

An image displayed by the notification system described in above-mentioned PTL 1 (image based on processed information described above) shows the action levels of the sympathetic nerves and the parasympathetic nerves in the form of graphs, but the graphs undesirably allow a user to readily figure out the state of the autonomic nerves in an intuitive manner. On the other hand, it is conceivable to display an image showing a sentence that describes the state of the autonomic nerves. In the case where such an image is displayed, however, the user naturally needs to read the sentence, which also does not allow the user to readily figure out the state of the autonomic nerves in an intuitive manner. It is therefore desired to generate an image so configured that it allows the user to readily figure out the state of the autonomic nerves.

An advantage of some aspects of the invention is to provide an image display apparatus, a display control method, and a display control program that readily allow recognition of the state of the autonomic nerves.

Solution to Problem

An image display apparatus according to an aspect of the invention is an image display apparatus that displays a biological state image showing the state of autonomic nerves based on detected biological information and includes a display section that displays an image, an information acquisition section that acquires predominance levels of sympathetic nerves and parasympathetic nerves and an activity magnitude of the autonomic nerves based on the biological information, an image generation section that generates the biological state image in which a figure having a size according to the acquired activity magnitude of the autonomic nerves is set along a first axis, along one side of which the predominance level of the sympathetic nerves is set with respect to a reference point and along the other side of which the predominance level of the parasympathetic nerves is set with respect to the reference point, in a position according to the acquired predominance levels of the sympathetic nerves and the parasympathetic nerve, and a display control section that causes the display section to display the generated biological state image.

According to the aspect of the invention, the position and size of a figure in the biological state image generated by the image generation section show the predominance levels of the sympathetic nerves and the parasympathetic nerves and the activity magnitude of the autonomic nerves. As a result, which of and how much the sympathetic nerves or the parasympathetic nerves are dominant can be intuitively figured out as compared with the image described above that shows the activity levels of the sympathetic nerves and the parasympathetic nerves in the form of graphs and the image described above that describes the state of the autonomic nerves in the form of a sentence. Further, the activity magnitude of the autonomic nerves can be readily figured out. The state of the autonomic nerves can therefore be readily figured out.

In the aspect of the invention, it is preferable in the biological state image generated by the image generation section that the figure is set along the first axis whenever the predominance levels of the sympathetic nerves and the parasympathetic nerves and the activity magnitude of the autonomic nerves are acquired, and that a portion where the figure overlaps with another figure has a color deeper than the color of a portion where the figures do not overlap with each other.

The biological state image can be an image in which figures are arranged in accordance with the predominance levels and the activity magnitude described above acquired within a predetermined period, and the predetermined period can, for example, be one day, several hours, or several minutes.

According to the aspect of the invention, whenever biological information is acquired and the predominance levels and the activity magnitude described above are acquired from the biological information, a figure showing the predominance levels and the activity magnitude is set along the first axis. As a result, the distribution of the predominance levels and the activity magnitude can be figured out based on the figures set in the biological state image. The balance between the sympathetic nerves and the parasympathetic nerves within the predetermined period can therefore be figured out.

Further, since a portion where figures overlap with each other shows a deep color, whereas a portion where figures do not overlap with each other shows a light color, the degree of overlap between the figures can be determined. The degree of the overlap therefore allows visual recognition of the distribution and tendency of the predominance levels and the activity magnitude described above and hence determination of whether or not the state of the autonomic nerves is normal.

Instead, in the aspect of the invention, it is preferable in the biological state image generated by the image generation section that whenever the predominance levels of the sympathetic nerves and the parasympathetic nerves and the activity magnitude of the autonomic nerves are acquired, the figure having a size according to the acquired activity magnitude is set not only along the first axis and in a position according to the acquired predominance levels of the sympathetic nerves and the parasympathetic nerves but also along a second axis which intersects the first axis and along which time is set and in a position according to the time at which the predominance levels and the activity magnitude are acquired.

According to the aspect of the invention, in the generated biological state image, a figure showing the predominance levels of the sympathetic nerves and the parasympathetic nerves and the activity magnitude of the autonomic nerves is set along the second axis in a position according to the time at which the predominance levels and the activity magnitude are acquired. As a result, temporal changes in the predominance levels and the activity magnitude described above can be figured out based on the biological state image. The state of the autonomic nerves can therefore be more accurately figured out.

Instead, in the aspect of the invention, the image generation section preferably generates the following images as the biological state image whenever the predominance levels of the sympathetic nerves and the parasympathetic nerves and the activity magnitude of the autonomic nerves are acquired: a first image in which the figure is set along the first axis and a portion where the figure overlaps with another figure has a color deeper than the color of a portion where the figures do not overlap with each other; and a second image in which the figure having a size according to the acquired activity magnitude is set not only along the first axis and in a position according to the acquired predominance levels of the sympathetic nerves and the parasympathetic nerves but also along a second axis which intersects the first axis and along which time is set and in a position according to the time at which the predominance levels and the activity magnitude are acquired, and the display control section preferably switches an image to be displayed in the display section between the first image and the second image generated by the image generation section in response to operation performed on the image display apparatus.

An example of the operation performed on the image display apparatus described above is, in a case where an operation unit, such as buttons, is provided, input operation performed on the operation unit. In a case where a detection unit that detects the attitude of the image display apparatus is provided, operation of changing the attitude is an example of the operation.

According to the aspect of the invention, the display control section switches an image displayed in the display section in accordance with user's operation performed on the image display apparatus between the first image, which allows the user to figure out the distribution and tendency of the predominance levels and the activity magnitude described above, and the second image, which allows the user to figure out temporal changes in the predominance levels and the activity magnitude, whereby the user can figure out the state of the autonomic nerves in more detail.

A display control method according to another aspect of the invention is a display control method for displaying a biological state image showing the state of autonomic nerves based on detected biological information, the method including acquiring predominance levels of sympathetic nerves and parasympathetic nerves and an activity magnitude of the autonomic nerves based on the biological information and displaying the biological state image in which a figure having a size according to the acquired activity magnitude of the autonomic nerves along a first axis, along one side of which the predominance level of the sympathetic nerves is set with respect to a reference point and along the other side of which the predominance level of the parasympathetic nerves is set with respect to the reference point, in a position according to the acquired predominance levels of the sympathetic nerves and the parasympathetic nerves.

The aspect of the invention can provide the same advantageous effects as those provided by the image display apparatus described above.

A display control program according to another aspect of the invention is a display control program executed by an image display apparatus that displays a biological state image showing the state of autonomic nerves based on detected biological information and causing the image display apparatus to display the biological state image, the program causing the image display apparatus to acquire predominance levels of sympathetic nerves and parasympathetic nerves and an activity magnitude of the autonomic nerves based on the biological information and to display the biological state image in which a figure having a size according to the acquired activity magnitude of the autonomic nerves along a first axis, along one side of which the predominance level of the sympathetic nerves is set with respect to a reference point and along the other side of which the predominance level of the parasympathetic nerves is set with respect to the reference point, in a position according to the acquired predominance levels of the sympathetic nerves and the parasympathetic nerves.

According to the aspect of the invention, the same advantageous effects as those provided by the image display apparatus described above can be provided when the image display apparatus executes the display control program.

DESCRIPTION OF EMBODIMENT

[First Embodiment]

A first embodiment of the invention will be described below with reference to the drawings.

[Configuration of Image Display Apparatus]

Figure 1:
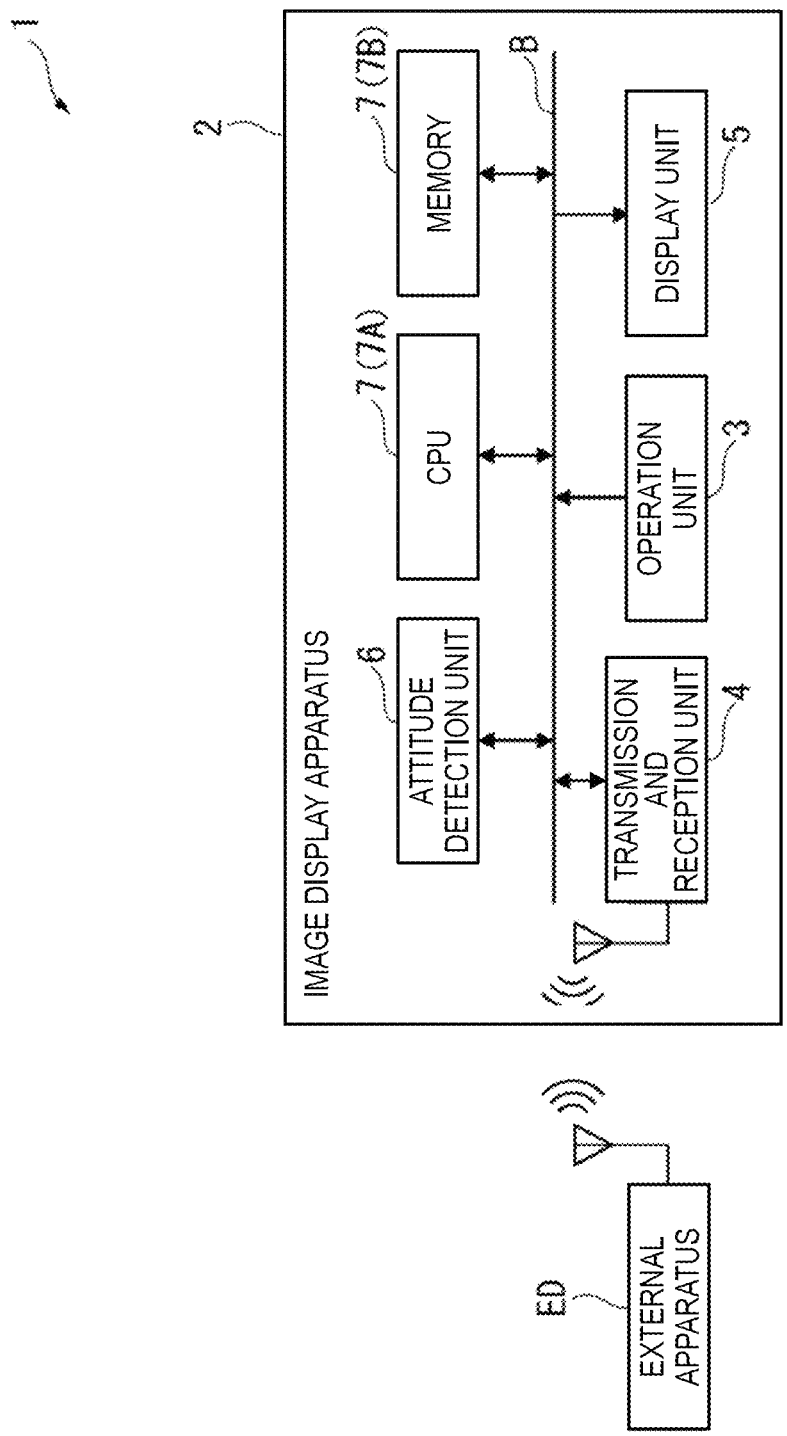
FIG. 1 is a hardware block diagram showing the configuration of an image display apparatus according to a first embodiment of the invention.

FIG. 1 is a block diagram showing the configuration of an image display apparatus 1 according to the present embodiment.

The image display apparatus 1 according to the present embodiment displays a biological state image showing a biological state (in detail, state of autonomic nerves). The image display apparatus 1 communicates with an external apparatus ED as shown in FIG. 1 and generates and displays a biological state image based on information received from the external apparatus ED.

In the present embodiment, the external apparatus ED acquires, for example, the pulse (heart rate), which is biological information, from a human body to which the external apparatus ED is attached, performs frequency analysis on the pulse to derive changes therein, and substitutes the result of the analysis into a predetermined computation expression to acquire information containing predominance levels of the sympathetic nerves and the parasympathetic nerves, which form the autonomic nerves, and the activity magnitude of the autonomic nerves. The external apparatus ED then transmits the acquired information and the date and time when the biological information is acquired to the image display apparatus 1.

The image display apparatus 1 includes an operation unit 3, a transmission and reception unit 4, a display unit 5, an attitude detection unit 6, and a control unit 7, which are connected to each other via a bus line B, and further includes an enclosure 2, which accommodates the components described above. The image display apparatus 1 is configured as a smartphone, a tablet terminal, or any other portable, compact terminal in the present embodiment but is not limited thereto and may be a desktop image display apparatus, such as a PC (personal computer).

The operation unit 3 is formed, for example, of a keyboard or a pointing device and outputs an operation signal according to input operation to the control unit 7.

The transmission and reception unit 4 communicates with the external apparatus ED to transmit and receive information to and from the external apparatus ED. In the present embodiment, the transmission and reception unit 4 receives information containing the predominance levels and the activity magnitude described above and outputs the information to the control unit 7. It is noted that the transmission and reception unit 4 and the external apparatus ED wirelessly communicate with each other in the present embodiment, but wireless communication is not necessarily employed and they may be wired to each other for communication.

The display unit 5 corresponds to the display section in an embodiment of the invention and displays an image according to an image signal inputted from the control unit 7. An image display area AR (see FIG. 5) of the display unit 5 has a rectangular shape. The thus configured display unit 5 can be a liquid crystal panel, an organic EL (electro-luminescence) panel, a plasma panel, or any of a variety of other display devices.

The attitude detection unit 6 detects the attitude of the enclosure 2. Specifically, the attitude detection unit 6 includes a sensor (acceleration sensor or gyro sensor, for example) that detects the attitude of the enclosure 2, and the attitude detection unit 6 detects whether the display area AR of the display unit 5 is vertically elongated (see FIG. 8A) or horizontally elongated (see FIG. 8B). The attitude detection unit 6 then outputs a signal representing the attitude of the enclosure 2 to the control unit 7.

[Configuration of Control Unit]

Figure 2:
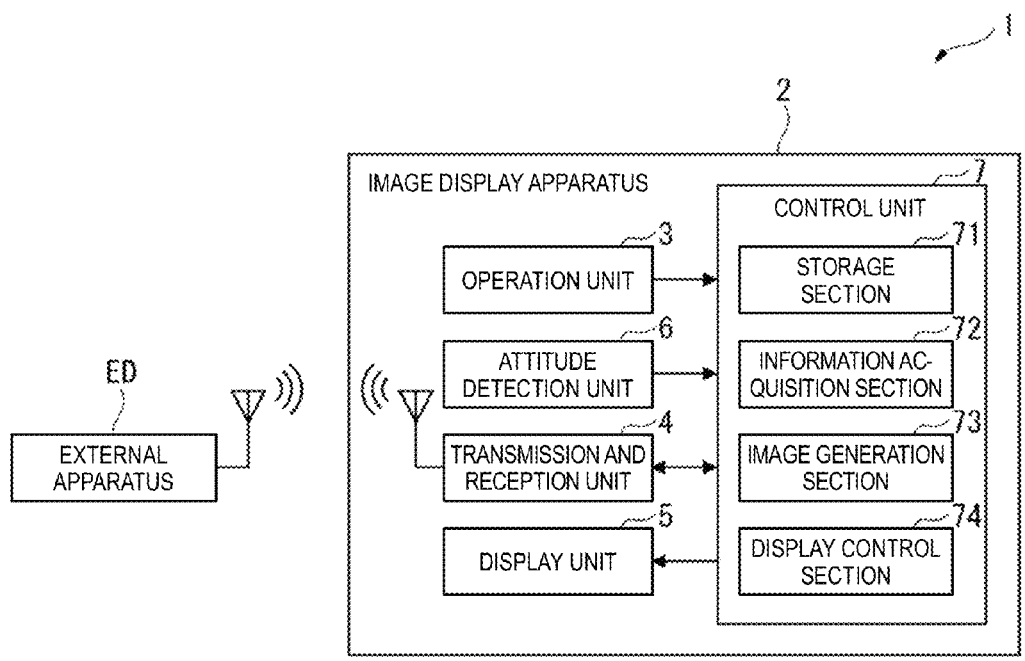
FIG. 2 is a functional block diagram showing the configuration of the image display apparatus in the first embodiment.

FIG. 2 is a functional block diagram showing the configuration of the control unit 7.

The control unit 7 is formed, for example, of a CPU (central processing unit) 7A and a memory 7B and controls the action of the image display apparatus 1 based on user's operation performed on the operation unit 3 or in an autonomous manner. For example, the control unit 7 generates a biological state image based on information received from the external apparatus ED and instructs the display unit 5 to display the biological state image.

The thus configured control unit 7 includes a storage section 71 formed of the memory 7B described above. The control unit 7 further functions as an information acquisition section 72, an image generation section 73, and a display control section 74, which are implemented when the CPU 7A described above executes a program stored in the storage section 71, as shown in FIG. 2.

The storage section 71 is formed, for example, of a flash memory or an HDD (hard disk drive) and stores a variety of programs and data necessary for the image display apparatus 1 to operate. One of the programs stored in the storage section 71 is a control program for carrying out a display control process, which will be described later. The data stored in the storage section 71 are, for example, a variety of pieces of information received from the transmission and reception unit 4.

The information acquisition section 72 controls the transmission and reception unit 4 to cause it to receive a variety of pieces of information transmitted from the external apparatus ED. The information acquisition section 72 then causes the storage section 71 to store the received information. The information acquisition section 72 regularly (every 30 minutes, for example) acquires the information described above from the external apparatus ED through the transmission and reception unit 4 and acquires the predominance levels and the activity magnitude described above contained in the acquired information.

The image generation section 73 generates (draws) an image to be displayed by the display unit 5. The image generation section 73 further generates a biological state image based on the information acquired by the information acquisition section 72 in response to user's input operation performed on the operation unit 3.

[Configuration of Summed Image]

Figure 3:
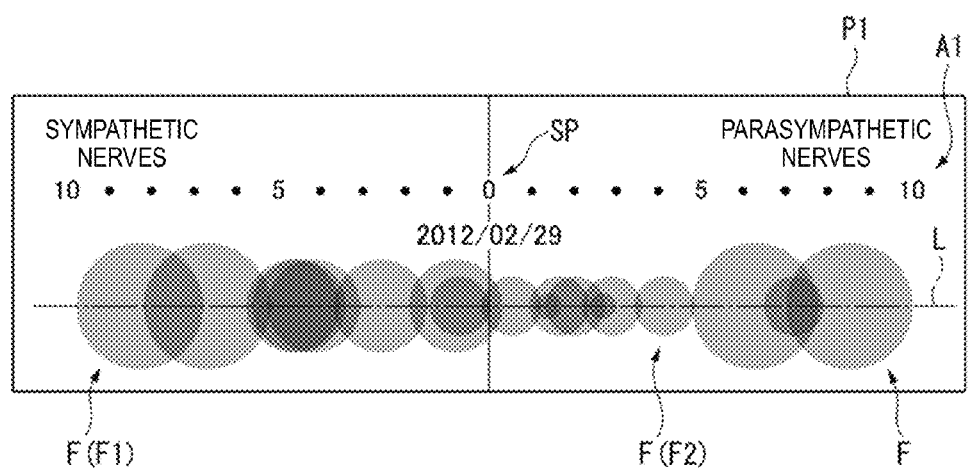
FIG. 3 shows an example of a summed image in the first embodiment.

FIG. 3 shows an example of a summed image P1 contained in a biological state image. In the following drawings, some of reference characters that denote figures F are omitted for ease of illustration.

The image generation section 73 generates a summed image P1 (see FIG. 3) and a time-series image P2 (see FIG. 7), which will be described below, as the biological state image.

Figure 8A:
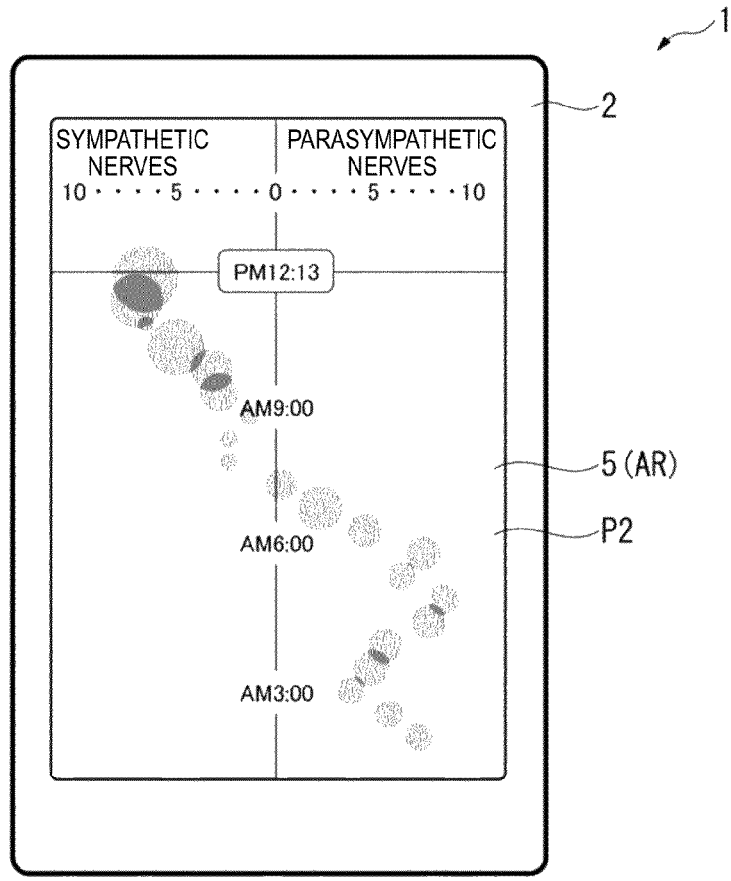
FIGS. 8A and 8B show switching a biological state image to another in the first embodiment.
Figure 8B:
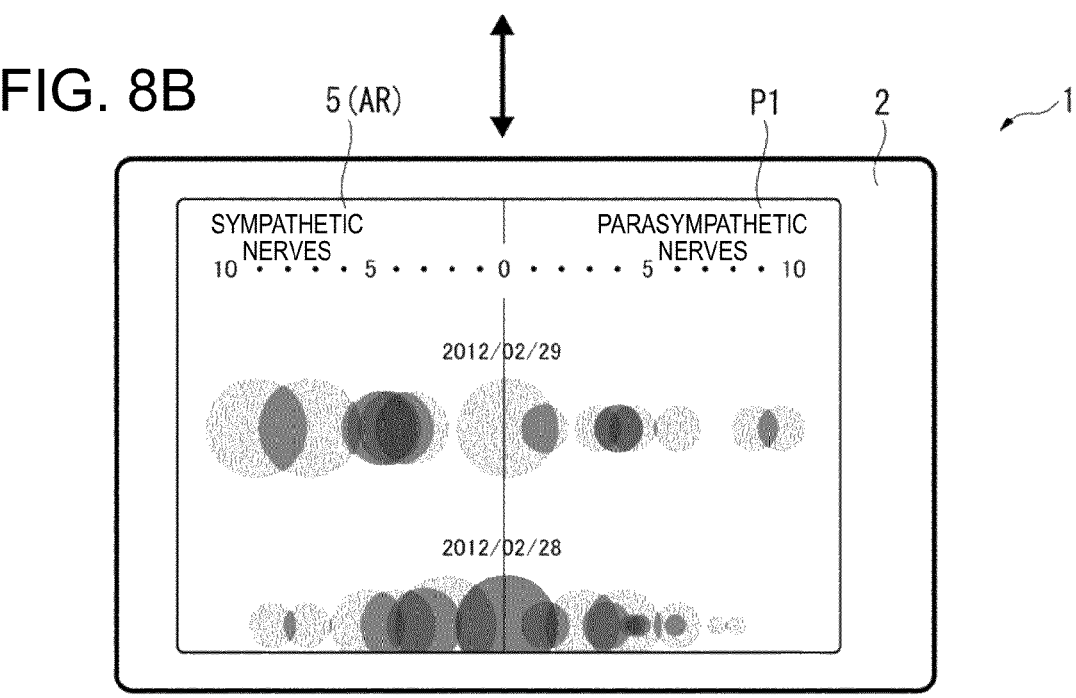

The summed image P1 is an image displayed when the display area AR of the display unit 5 is horizontally elongated (see FIG. 8(B)) and showing the predominance levels and the activity magnitude described above based on biological information detected within a predetermined period (one day, for example) and in the form of predetermined figures F (circles in the present embodiment) as shown in FIG. 3. The summed image P1 corresponds to the first image in an embodiment of the invention.

In the summed image P1, a level axis A1 (first axis), which extends along the longitudinal direction of the display area AR, is set, and markings indicating the predominance level of the sympathetic nerves and the predominance level of the parasympathetic nerves are set along the level axis A1. Specifically, with respect to a reference point SP (position where numeral of "0" is set) at the center of the level axis A1, markings indicating the predominance level of the sympathetic nerves are set in the form of numerals ranging from 1 to 10 on one side (left side) of the level axis A1, and markings indicating the predominance level of the parasympathetic nerves are set in the form of numerals ranging from 1 to 10 on the other side (right side) of the level axis A1. The date when the biological information is acquired is also set in the summed image P1.

In the summed image P1, whenever the information acquisition section 72 acquires information containing the predominance levels and the activity magnitude described above, a figure F having a dimension according to the acquired activity magnitude is set on the level axis A1 in a position corresponding to the acquired predominance levels. Each figure F is so disposed that the center thereof is located on an imaginary straight line L extending along the level axis A1.

For example, when the acquired information contains information representing that "the predominance level of the sympathetic nerves is 8.2" and information representing that "the activity magnitude of the autonomic nerves is 4," a figure F (F1) having a size corresponding to the activity magnitude of 4 is set on the straight line L described above in a position where the predominance level of the sympathetic nerves is "8.2".

When the acquired information contains information representing that "the predominance level of the parasympathetic nerves is 4.1" and information representing that "the activity magnitude of the autonomic nerves is 2," a figure F (F2) having a size corresponding to the activity magnitude of 2 is set on the straight line L described above in a position where the predominance level of the parasympathetic nerves is "4.1".

In the thus configured summed image P1, a new figure F may be set in some cases in a position where the new figure F overlaps with a figure F having already been set. In view of the circumstances described above, a figure F set in the summed image P1 has preset transmittance. As a result, an area where figures F do no overlap with each other is expressed in a light density color, whereas an area where figures F overlap with each other is expressed in a deep density color. The color density thus indicates the degree of overlap between figures F, whereby the distribution and tendency of the predominance levels and the activity magnitude described above in a predetermined period can be figured out.

For example, within a range of "the predominance level of the parasympathetic nerves from 4 to 5" in FIG. 3, one figure F having its center located within the range is set. This indicates that biological information representing that "the predominance level of the parasympathetic nerves ranges from 4 to 5" has been acquired once on a date of "2012/02/29."

On the other hand, within a range of "the predominance level of the sympathetic nerves ranging from 0 to 1," two figures F having their centers located within the range are set. This indicates that biological information representing that "the predominance level of the sympathetic nerves ranges from 0 to 1" has been acquired twice on the date of "2012/02/29."

The color of a figure F is set in accordance with the type and the predominance level of a dominant one of the two types of autonomic nerves.

That is, when acquired information contains a predominance level of the sympathetic nerves, it is determined that "the sympathetic nerves are dominant" and a warm color (red, yellow, or orange, for example) is set as the color of a figure F to be set. Further, a warmer color (that is, color shifted from yellow toward red) is set as the color of the figure F as the predominance level of the sympathetic nerves increases.

On the other hand, when acquired information contains a predominance level of the parasympathetic nerves, it is determined that "the parasympathetic nerves are dominant" and a cold color (blue or color close to blue, for example) is set as the color of a figure F to be set. Further, a colder color (that is, color shifted from green toward blue) is set as the color of the figure F as the predominance level of the parasympathetic nerves increases.

A warm color is believed to visually act on the sympathetic nerves of the person who is looking at the color and increase the person's emotion. On the other hand, a cold color is believed to visually act on the parasympathetic nerves of the person who is looking at the color and lower the person's excitement. Therefore, using a warm color as the color of a figure F when the sympathetic nerves are dominant whereas using a cold color as the color of a figure F when the parasympathetic nerves are dominant allows the user to intuitively figure out which is dominant, the sympathetic nerves or the parasympathetic nerves. The state of the autonomic nerves can therefore be more readily and appropriately figured out.

When acquired information contains information representing "a predominance level of zero," a gray figure F is set in the position corresponding to the reference point SP at the center of the level axis A1.

When the thus configured summed image P1 is displayed, summed images P1 for the past few days before the date of the summed image P1 are also displayed. That is, although FIG. 3 shows only a summed image P1 on "2012/02/29," summed images P1 for the past few days (one week, for example) including "2012/02/29" are actually displayed, as shown in FIG. 8B. After a summed image P1 is displayed, the user can scroll the display area of the display unit 5 to observe summed images P1 on the other dates.

Figure 4:
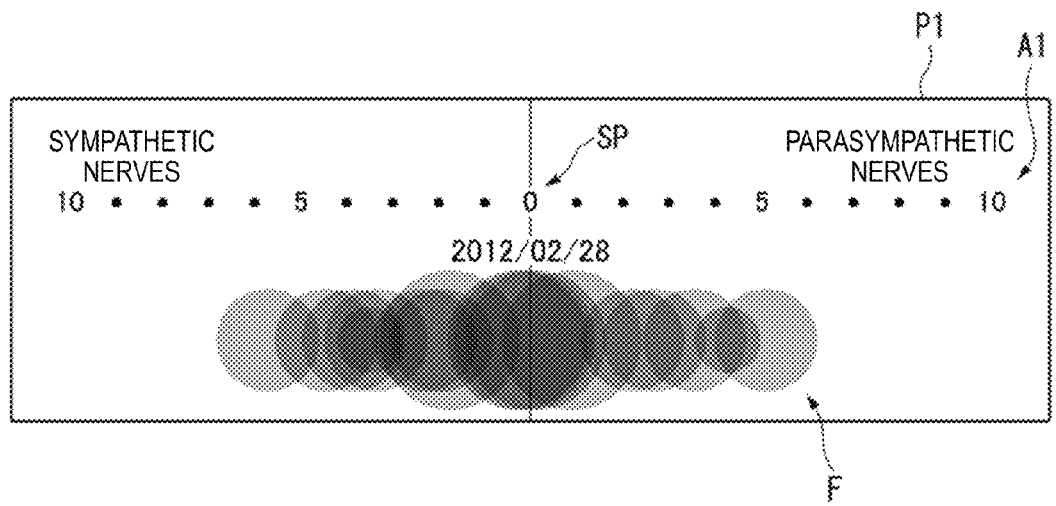
FIG. 4 shows another example of the summed image in the first embodiment.
Figure 5:
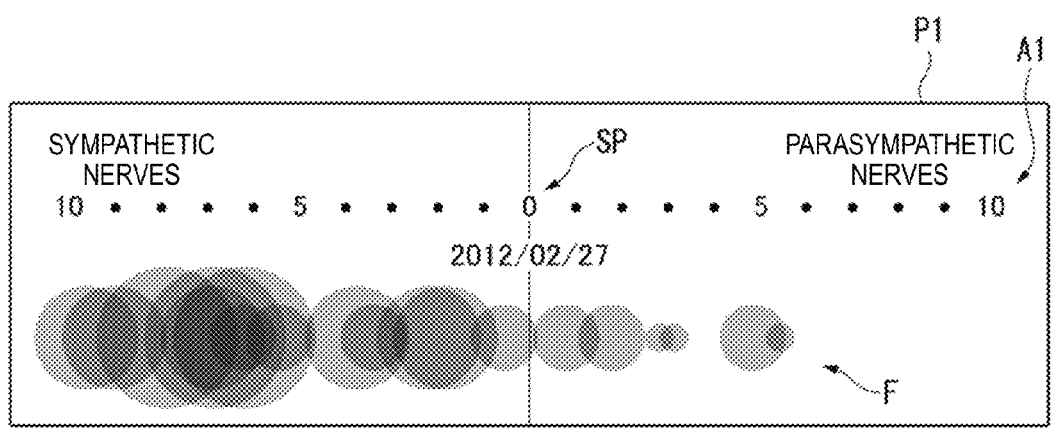
FIG. 5 shows another example of the summed image in the first embodiment.
Figure 6:
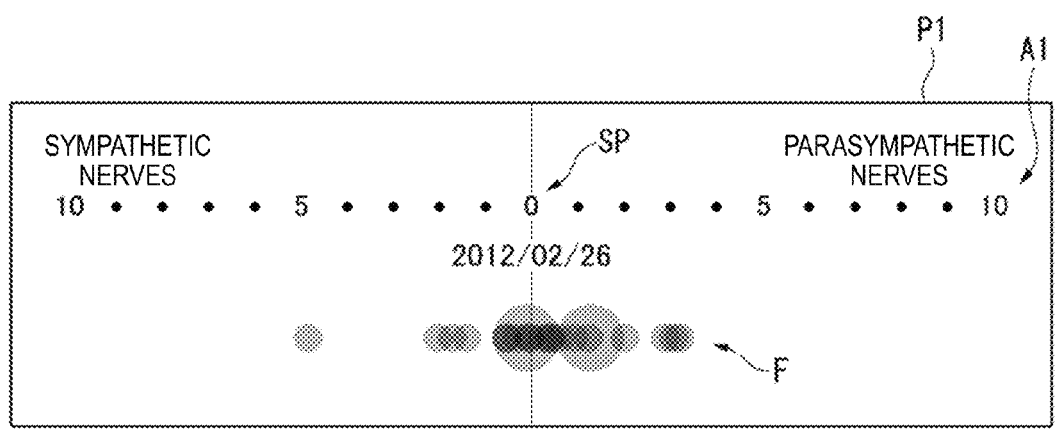
FIG. 6 shows another example of the summed image in the first embodiment.

FIGS. 4 to 6 show other examples of the summed image P1.

The following points can be figured out from the summed images P1 shown in FIGS. 4 to 6.

For example, in a summed image P1 labeled with "2012/02/28" shown in FIG. 4, figures F each having a relatively large dimension are disposed along the level axis A1 within a relatively wide range centered around the reference point SP.

In general, the activity magnitude is higher in a healthier person (greater dimension of figure F), and the sympathetic nerves and the parasympathetic nerves act in a better balanced manner. The state shown in FIG. 4 is therefore not only a state classified into a healthy state but also a state in which the autonomic nerves satisfactorily function.

On the other hand, in a summed image P1 labeled with "2012/02/27" shown in FIG. 5, each figure F disposed in FIG. 5 is shifted to the sympathetic-nerve side of the level axis A1. In a summed image P1 labeled with "2012/02/26" shown in FIG. 6, figures F each having a relatively small dimension are concentrated in a relatively narrow range centered around the reference point SP of the level axis A1. A state in which the predominance level does not change but is shifted to the sympathetic-nerve side or the parasympathetic-nerve side and a state in which the activity magnitude of the autonomic nerves is small are classified into an unhealthy state. The states of the autonomic nerves shown in FIGS. 5 and 6 are therefore not normal.

As described above, a summed image P1 based on biological information acquired within a predetermined period (one day in the present embodiment) allows determination of whether or not the state of the autonomic nerves is normal.

[Configuration Time-series Image]

Figure 7:
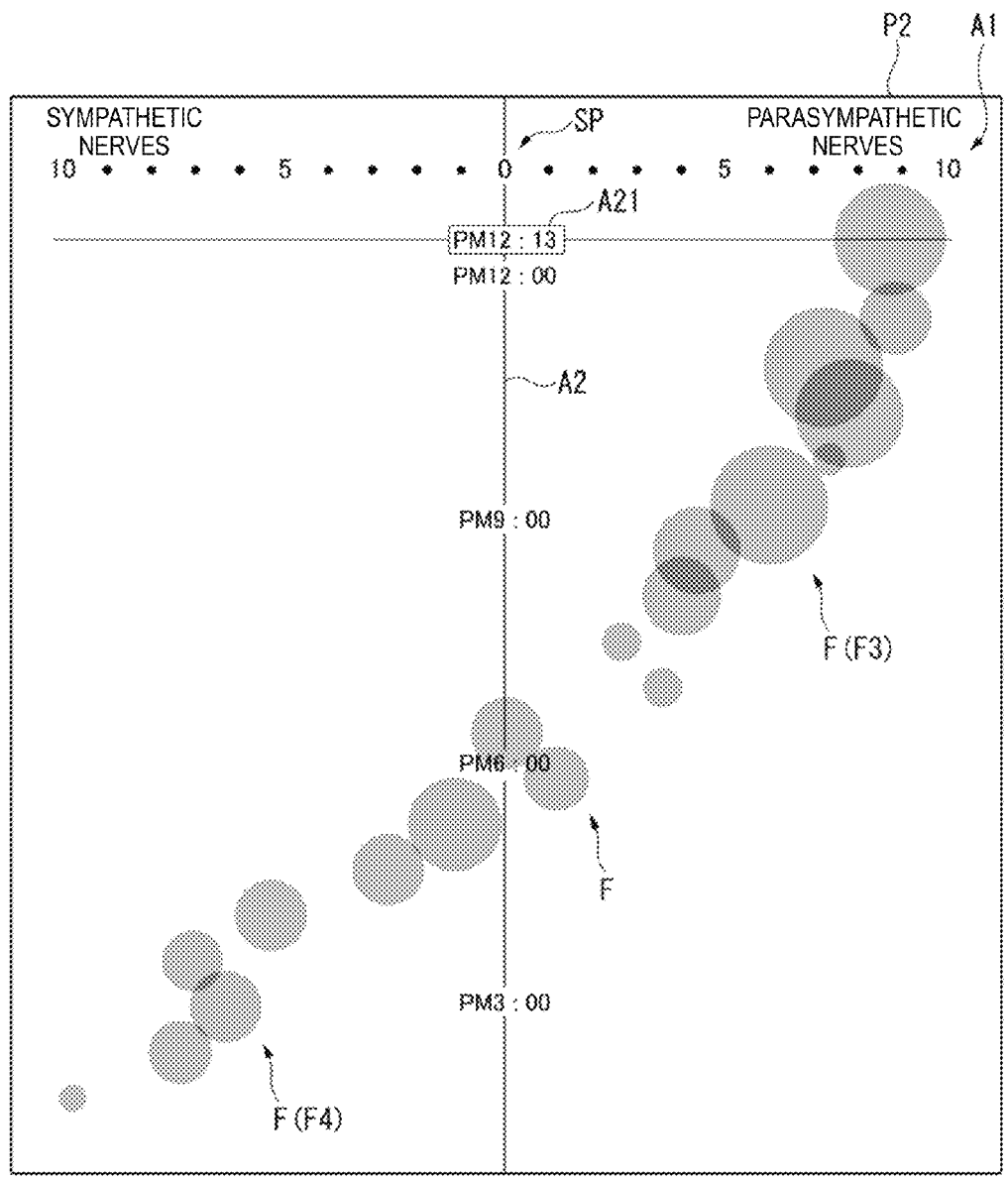
FIG. 7 shows an example of a time-series image in the first embodiment.

FIG. 7 shows an example of the time-series image P2 contained in a biological state image.

The time-series image P2 is an image displayed when the display area AR of the display unit 5 is vertically elongated (see FIG. 8A), and whenever biological information is acquired, a figure F according to the biological information is set in a time-series manner in the time-series image P2 as shown in FIG. 7. The time-series image P2 corresponds to the second image in an embodiment of the invention.

In the present embodiment, the time-series image P2 is a vertically elongated image in which figures F are set in accordance with the predominance levels and the activity magnitude described above based on biological information for the past few days (three days, for example) before the date and time selected by the user, and the display control section 74, which will be described later, displays part of the time-series image P2 in the display unit 5. When the user operates the operation unit 3 to scroll the time-series image P2 upward or downward (when the user scrolls the time-series image P2 along a temporal axis A2), the display control section 74 displays an area of the scrolled time-series image P2. When the user has not selected the date and time when a time-series image P2 to be displayed is acquired, a time-series image P2 according to the predominance levels and the activity magnitude described above acquired within a period corresponding to the past few days before the current time is generated and displayed.

The thus formed time-series image P2 has the following axes set therein: a level axis A1 extending along the short sides of the time-series image P2; and a temporal axis A2 (second axis) extending along the long sides thereof. That is, the level axis A1 and the temporal axis A2 intersect each other at the reference point SP of the level axis A1.

The temporal axis A2 is accompanied by a time setting area A21, where the current time is set, and markings indicating past time with respect to the current time are set along the temporal axis A2 (time markings are set every 3 hours for past 10 hours in FIG. 7).

The level axis A1 is always displayed even when the time-series image P2 is scrolled upward or downward. On the other hand, each of the past time markings set along the temporal axis A2 is moved in the direction away from the level axis A1 when the current time is updated, and the figure F set in accordance with the past time is also moved in the same direction accordingly.

In the time-series image P2, a figure F is so set that it has a dimension according to the activity magnitude of the autonomic nerves and is located in a position along the temporal axis A2 according not only to the time at which biological information is acquired but also to the predominance levels of the sympathetic nerves and the parasympathetic nerves based on the biological information.

For example, when information on the predominance levels of the sympathetic nerves and the parasympathetic nerves representing that "the predominance level of the parasympathetic nerves is 6.0" and information on the activity magnitude of the autonomic nerves representing that "the activity magnitude is 4" are acquired based on biological information acquired at "9:00 PM," a figure F (F3) having a size according to the "activity magnitude of 4" is set in a position according not only to "9:00 PM" on the temporal axis A2 but also to "the predominance level of the parasympathetic nerves of 6.0" on the level axis A1.

On the other hand, when information representing that "the predominance level of the sympathetic nerves is 6.3" and information representing that "the activity magnitude of the autonomic nerves is 2" are acquired based on biological information acquired at "3:00 PM," a figure F (F4) having a size according to the "activity magnitude of 2" is set in a position according not only to "3:00 PM" on the temporal axis A2 but also to "the predominance level of the sympathetic nerves of 6.3" on the level axis A1.

The thus configured time-series image P2 shows the time at which biological information is acquired and the contents of the biological information. In the time-series image P2, the color and transmittance of a set figure F are the same as those in the summed image P1 described above.

The thus generated and displayed time-series image P2 allows the user to figure out a temporal change in the autonomic nerves as well as the time at which the change occurs. As a result, for example, a difference between the state of the autonomic nerves of the user and the state of normal autonomic nerves, which have a tendency in which the sympathetic nerves are dominant in the daytime whereas the parasympathetic nerves are dominant at night, can also be figured out, whereby whether or not the state of the autonomic nerves of the user is normal can be determined.

FIGS. 8A and 8B show the summed image P1 and the time-series image P2 switched from one to the other in accordance with the attitude of the enclosure 2.

The summed image P1 and the time-series image P2 are switched from one to the other by the display control section 74. The display control section 74 causes the display unit 5 to display an image generated by the image generation section 73 (biological state image described above as well as image showing state of image display apparatus 1).

For example, the display control section 74 causes the display unit 5 to display a time-series image P2 when the display control section 74 determines that the display area AR of the display unit 5 is vertically elongated when viewed from the user side based on a detection signal inputted from the attitude detection unit 6, as shown in FIG. 8A.

On the other hand, the display control section 74 causes the display unit 5 to display a summed image P1 when the display control section 74 determines that the display area AR is horizontally elongated when viewed from the user side based on the detection signal.

Further, when the user operates the operation unit 3 to scroll a displayed image as described above, the display control section 74 reads the scrolled image in the display area and causes the display unit 5 to display the image.

The thus performed displayed image switching, specifically, for example, switching a displayed image between a summed image P1, which allows the user to figure out the state of the autonomic nerves on a daily basis, and a time-series image P2, which allows the user to figure out a temporal change in the state of the autonomic nerves in each day, allows the user to figure out the state of the autonomic nerves in more detail.

[Display Control Process]

Figure 9:
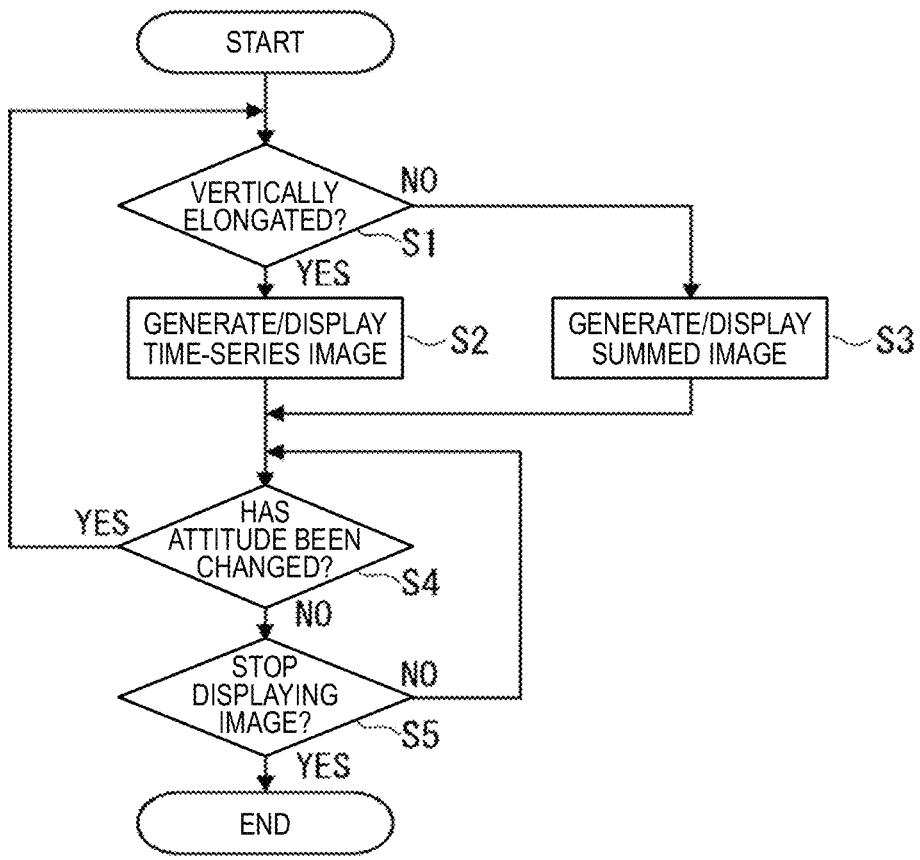
FIG. 9 is a flowchart showing a display control process in the first embodiment.

FIG. 9 is a flowchart showing a display control process carried out by the image display apparatus 1 (specifically, control unit 7).

In the image display apparatus 1 described above, when the user operates the operation unit 3 to display a biological state image, the CPU 7A, which forms the control unit 7, reads a display control program stored in the memory 7B (storage section 71) to carry out the following display control process.

In the display control process, the display control section 74 first determines whether or not the display area AR is vertically elongated based on a detection result from the attitude detection unit 6 (step Si), as shown in FIG. 9.

When the determination result in step Si shows that the display area AR is vertically elongated, the display control section 74 causes the image generation section 73 to generate the time-series image P2 described above and causes the display unit 5 to display the image P2 (step S2). The display control section 74 then proceeds to the process in step S4.

When the determination result in step Si shows that the display area AR is not vertically elongated (is horizontally elongated), the display control section 74 causes the image generation section 73 to generate the summed image P1 described above and causes the display unit 5 to display the image P1 (step S3). The display control section 74 then proceeds to the process in step S4.

In step S4, the display control section 74 determines, based on a signal inputted from the attitude detection unit 6, whether or not the attitude of the enclosure 2 has been changed. When the determination result in step S4 shows that the attitude of the enclosure 2 has been changed, the display control section 74 proceeds to the process in step S1.

On the other hand, when the determination result in step S4 shows that the attitude of the enclosure 2 has not been changed, the display control section 74 determines, based on an operation signal inputted from the operation unit 3, whether or not the user has operated the operation unit 3 to stop displaying the biological state image (step S5).

When the determination result in step S5 shows that the operation described above has not been performed, the display control section 74 proceeds to the process in step S4 and keeps displaying the biological state image.

When the determination result in step S5 shows that the operation described above has been performed, the display control section 74 stops displaying the biological state image, and the control unit 7 terminates the display control process. The display control section 74 then causes the display unit 5 to display an image showing the state of the image display apparatus 1.

The image display apparatus 1 according to the present embodiment described above provides the following advantageous effects:

(1) The position and size of a figure F in a biological state image (summed image P1 and time-series image P2) generated by the image generation section 73 show the predominance levels of the sympathetic nerves and the parasympathetic nerves and the activity magnitude of the autonomic nerves. As a result, which of and how much the sympathetic nerves or the parasympathetic nerves are dominant can be intuitively figured out as compared with the image described above that shows the activity levels of the sympathetic nerves and the parasympathetic nerves in the form of graphs and the image described above that describes the state of the autonomic nerves in the form of a sentence. Further, the activity magnitude of the autonomic nerves can be readily figured out. The state of the autonomic nerves can therefore be readily figured out.

(2) In the summed image P1 and the time-series image P2, whenever the predominance levels and the activity magnitude described above are acquired, a figure F showing the acquired information is set along the level axis A1. As a result, the distribution of the predominance levels and the activity magnitude can be figured out based on the position of each figure F set in each of the images P1 and P2. The balance between the sympathetic nerves and the parasympathetic nerves within a predetermined period can therefore be figured out.

Further, since a portion where figures F overlap with each other shows a deep color, whereas a portion where figures F do not overlap with each other shows a light color, the degree of overlap between the figures F can be determined. In the summed image P1, the degree of the overlap therefore allows the user to visually figure out the distribution and tendency of the predominance levels and the activity magnitude described above and hence determine whether or not the state of the autonomic nerves is normal.

(3) In the time-series image P2, a figure F showing the predominance levels and the activity magnitude described above is set along the temporal axis A2 in a position according to the time at which corresponding biological information is acquired. As a result, temporal changes in the predominance levels and the activity magnitude can be figured out. The state of the autonomic nerves can therefore be more accurately figured out.

(4) The display control section 74 switches an image displayed in the display unit 5 between the two types of images in accordance with the attitude of the enclosure 2 detected by the attitude detection unit 6. The displayed image switching, specifically, switching a displayed image between a summed image P1, which allows the user to figure out the distribution and tendency of the predominance levels and the activity magnitude described above on a daily basis, and a time-series image P2, which allows the user to figure out temporal changes in the predominance levels and the activity magnitude described above on a selected date, allows the user to figure out the state of the autonomic nerves in more detail.

[Variation of Summed Image]

Figure 10:
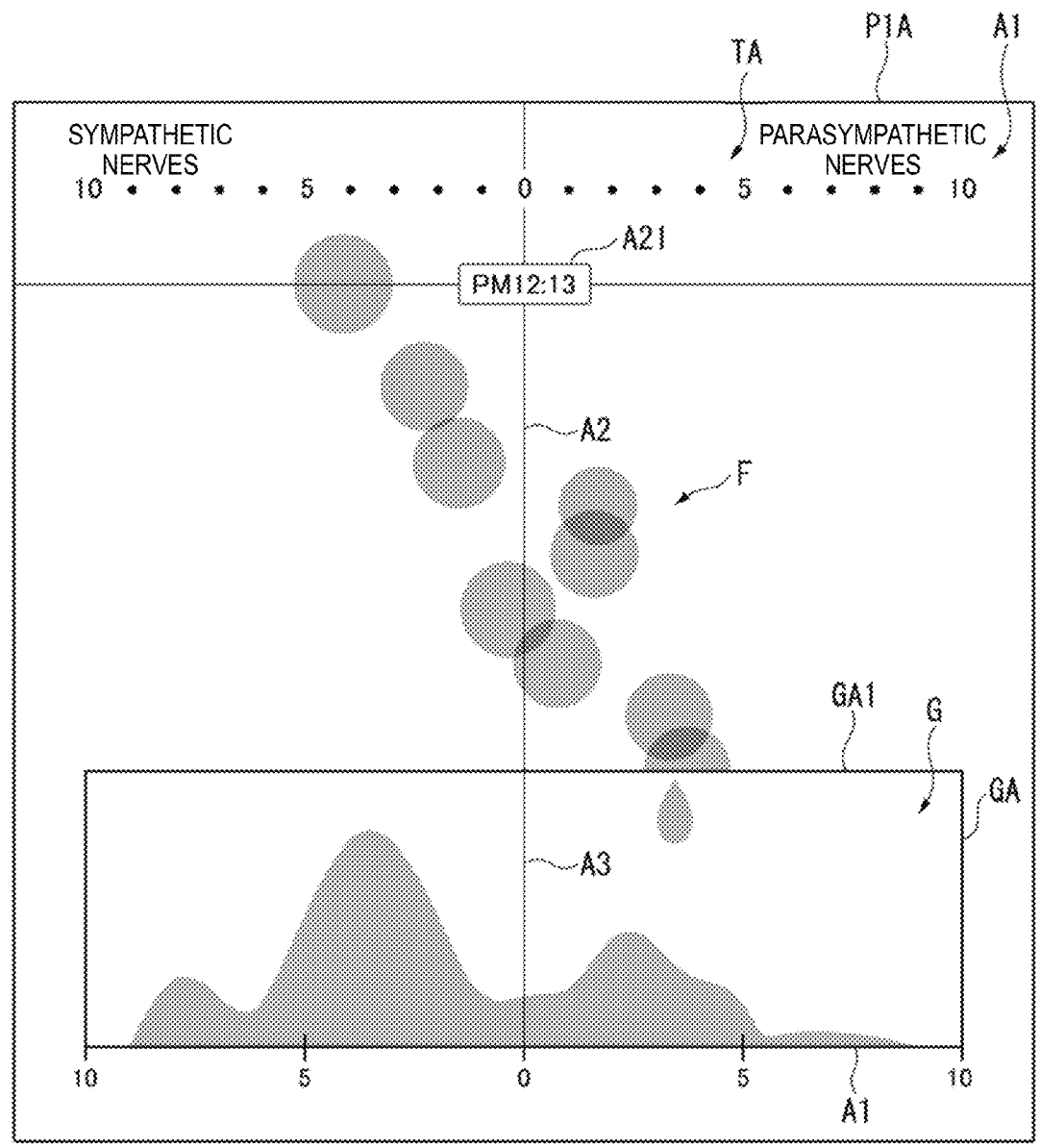
FIG. 10 shows still another example of the summed image in the first embodiment.

FIG. 10 shows another example of the summed image.

A summed image generated by the image generation section 73 is not limited to the summed image P1 described above and may be a summed image NA, which will be described below.

The summed image P1A is an image containing the contents of a time-series image P2 and the number of acquired pieces of biological information at each predominance level, and the summed image P1A has a time-series area TA and a graph area GA set therein, as shown in FIG. 10.

The time-series area TA, which is one of the two areas, has the level axis A1 and the temporal axis A2 set therein, as in the time-series image P2 described above. In the time-series area TA, a figure F having a dimension according to the activity magnitude of the autonomic nerves is set in a position according not only to the time at which the biological information described above is acquired but also to the predominance levels of the sympathetic nerves and the parasympathetic nerves. As a result, the predominance levels and the activity magnitude are shown in a time-series manner.

On the other hand, the graph area GA is located in the time-series area TA in a position on the front end side of the temporal axis A2 (on the side close to the past), and the graph area GA has the level axis A1 and a summation axis A3, which intersects the level axis A1, set therein. The summation axis A3 extends along the temporal axis A2.

In the graph area GA is set a graph G representing the summed number of acquired pieces of biological information representing each predominance level of the sympathetic and parasympathetic nerves. In other words, in the graph area GA is set a graph G representing the summed number of figures F set for each predominance level set based on biological information acquired within a predetermined period (one day, for example).

In the present embodiment, when an image in the time-series area TA is scrolled along the temporal axis A2 downward with time and a figure F set in the time-series area TA reaches an upper end GA1 of the graph area GA, the number of acquired pieces of biological information containing the predominance level indicated by the figure F is incremented, and the graph G is updated accordingly. At this point, animation images are generated in the graph area GA. In the animation, a drop falls onto the graph G in a position corresponding to the predominance level described above and the portion of the graph G in the position is lifted. Such an animation may be omitted, and a graph G according to pieces of biological information within a predetermined period including the latest biological information may instead be set.

The summed image NA described above also allows the user to visually figure out the distribution and tendency of the predominance levels within a predetermined period, whereby the same advantageous effects as those in the case where the summed image P1 and the time-series image P2 described above are displayed can be provided.

[Second Embodiment]

A second embodiment of the invention will be described below.

An image display apparatus according to the present embodiment differs from the image display apparatus 1 described above in that the image display apparatus according to the present embodiment has a configuration and function of directly acquiring biological information from a user who wears the image display apparatus and acquiring the predominance levels and the activity magnitude described above based on the acquired biological information. In the following description, the same or substantially the same portions as those having already been described have the same reference characters and no description of the portions will be made.

Figure 11:
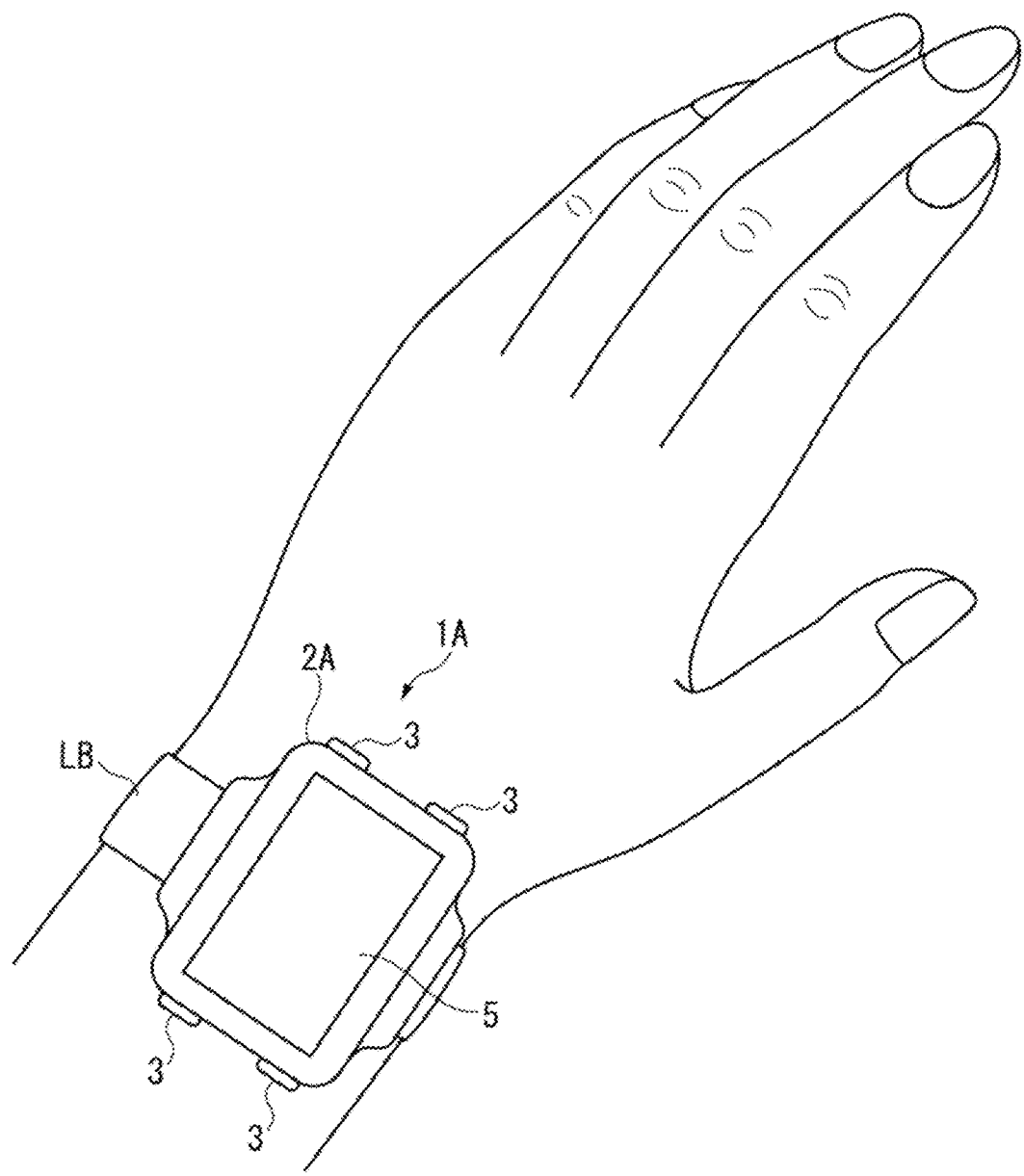
FIG. 11 is a perspective view showing an image display apparatus according to a second embodiment of the invention.
Figure 12:
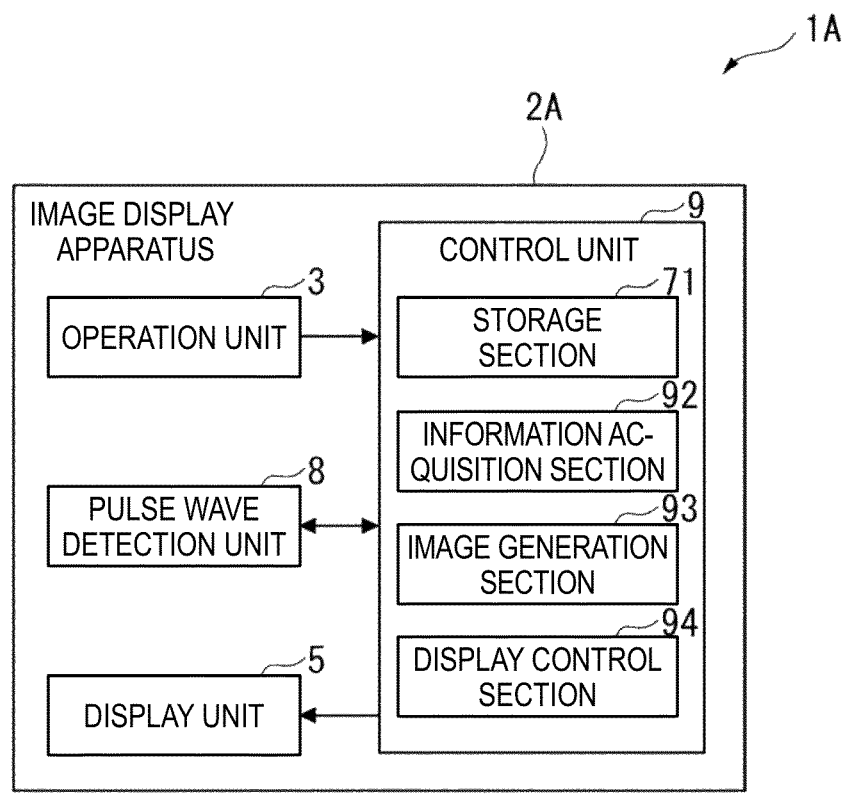
FIG. 12 is a functional block diagram showing the configuration of the image display apparatus in the second embodiment.

FIG. 11 is a diagrammatic view showing the exterior of an image display apparatus 1A according to the present embodiment. FIG. 12 is a block diagram showing the configuration of the image display apparatus 1A.

The image display apparatus 1A according to the present embodiment is worn, for example, around a wrist of a user as shown in FIG. 11 and generates and displays a biological state image showing the predominance levels and the activity magnitude described above based on biological information containing the pulse (heart rate) detected in a position where the image display apparatus 1A is worn. The image display apparatus 1A includes an enclosure 2A, which has a wristwatch-like shape and to which a wristband LB that allows the user to wear the image display apparatus 1A is attached. The image display apparatus 1A further includes the operation unit 3, the display unit 5, a pulse wave detection unit 8, and a control unit 9, as shown in FIG. 12.

The pulse wave detection unit 8 includes a photoelectric pulse wave sensor formed of an LED (light emitting diode) or any other light emitting device and a phototransistor or any other light receiving device. The pulse wave detection unit 8 outputs a blood flow pulse wave detected as the biological information to the control unit 9. The pulse wave detection unit 8 does not necessarily include the photoelectric pulse wave sensor and may include a pressure-based pulse wave detection sensor.

The control unit 9 includes the CPU 7A and the memory 7B and has the following functional sections achieved by the CPU 7A and the memory 7B: the storage section 71; an information acquisition section 92; an image generation section 93; and a display control section 94, as the control unit 7 described above does.

The information acquisition section 92 acquires biological information detected by the pulse wave detection unit 8 (that is, pulse wave) at a predetermined cycle (at a cycle of 30 seconds, for example). The acquisition of biological information performed by the information acquisition section 92 is autonomously performed without any special user's operation in the present embodiment but may instead be performed when the user operates the operation unit 3. Further, the cycle can be set by the user as appropriate.

The information acquisition section 92 performs frequency analysis on the acquired pulse wave to derive a change therein and substitutes the result of the analysis into a predetermined computation expression to acquire the predominance levels and the activity magnitude described above. The information acquisition section 92 then causes the storage section 71 to store the acquired predominance levels and activity magnitude along with the date and time when the pulse wave is detected.

Figure 13A:
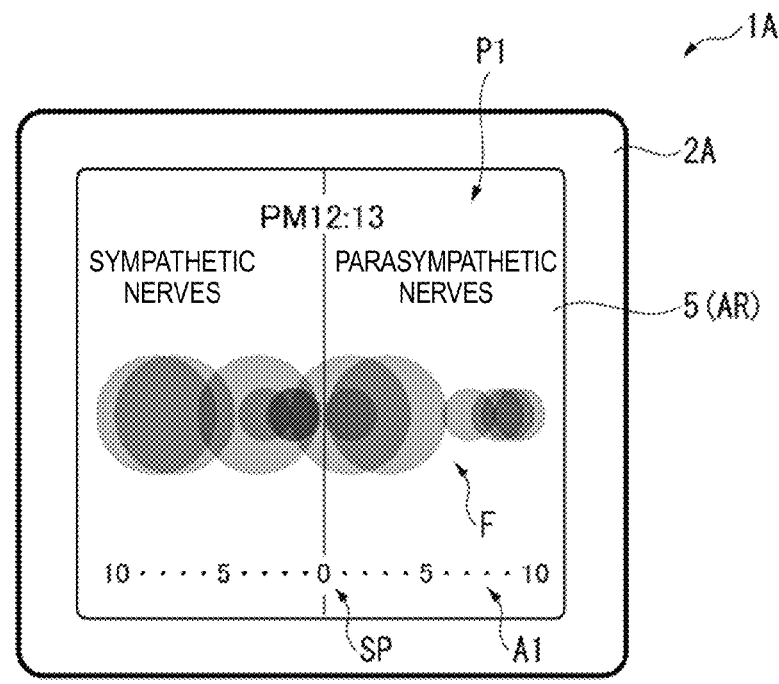
FIGS. 13A and 13B show switching a biological state image to another in the second embodiment.
Figure 13B:
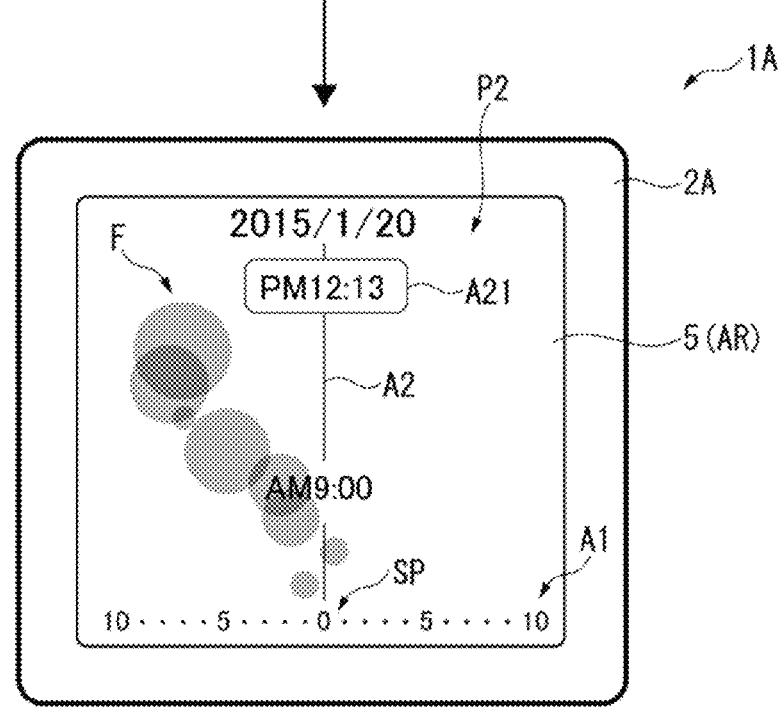

FIGS. 13A and 13B show switching a displayed image between the summed image P1 and the time-series image P2. FIG. 13A shows the image display apparatus 1A that displays the summed image P1, and FIG. 13B shows the image display apparatus 1A that displays the time-series image P2.

The image generation section 93 has the same function as that of the image generation section 73 described above, and when the user performs operation of displaying a biological state image, the image generation section 93 generates the biological state image (summed image P1 and time-series image P2) based on the information stored in the storage section 71.

In detail, the image generation section 93 according to the present embodiment generates a summed image P1 based on biological information within a predetermined period for the past 10 minutes before the current time, as shown in FIG. 13A. When new biological information is acquired during a period in which the summed image P1 is displayed, the image generation section 93 updates the summed image P1 based on the new biological information. At this point, a figure F based on biological information having been acquired for a period longer than 10 minutes may be sequentially deleted from the summed image P1.

Further, the predetermined period can be set as appropriate by the user. For example, a summed image P1 on a daily basis can be generated, as in the case of the summed image P1 shown in the first embodiment.

In addition, the date and time when biological information used by the image generation section 93 to generate the summed image P1 and the time-series image P2 (FIG. 13B) is acquired can be set by the user, as in the case of the image display apparatus 1 described above.

The display control section 94 causes the display unit 5 to display a biological state image containing the summed image P1 and the time-series image P2 in response to user's operation performed on the operation unit 3. In this process, the display control section 94 switches a displayed image between the image P1 and the image P2 based on the operation and displays the selected image, as shown in FIGS. 13A and 13B.

Since the image display apparatus 1A is worn around a wrist of the user as described above, the resolution of the display area AR of the display unit 5 is smaller than that of the image display apparatus 1. The images P1 and P2 displayed in the display area AR are therefore smaller than and laid out slightly differently from the images P1 and P2 generated by the image display apparatus 1. The user can, however, observe the entire images P1 and P2 by scrolling them, as in the case of the image display apparatus 1.

Figure 14:
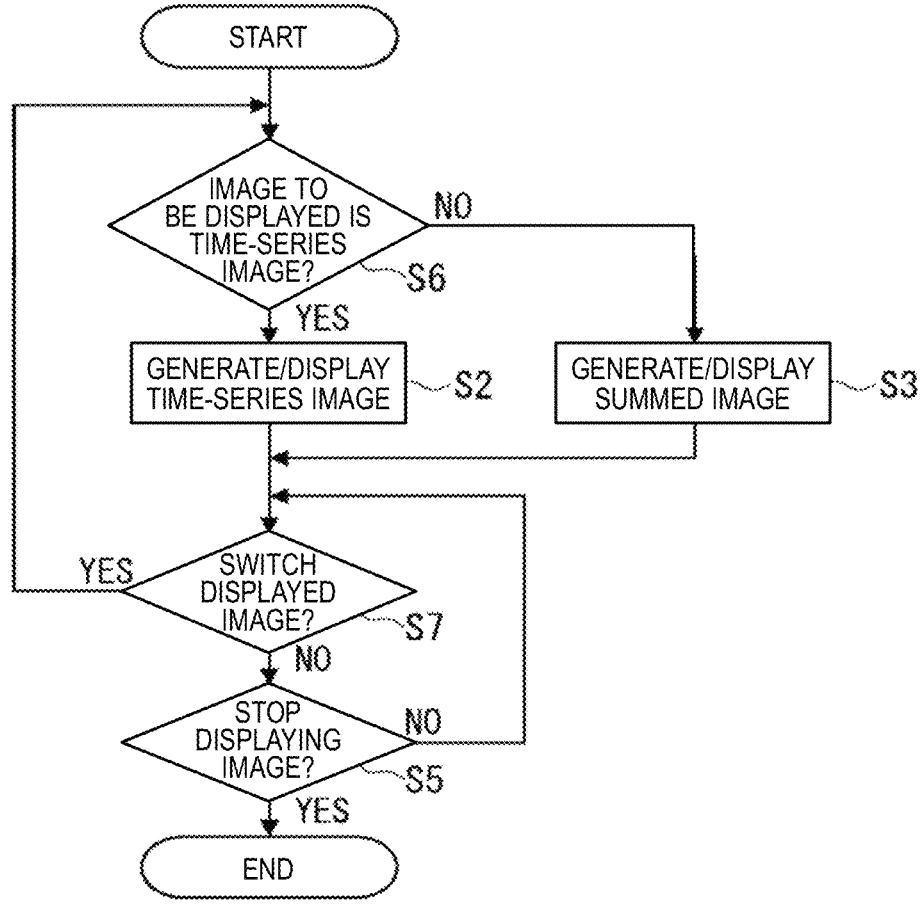
FIG. 14 is a flowchart showing a display control process in the second embodiment.

FIG. 14 is a flowchart showing the display control process in the image display apparatus 1A.

When the user operates the operation unit 3 to display a biological state image, the control unit 9 reads the display control program from the storage section 71 to carry out the following display control process.

In the display control process, the display control section 94 first determines whether or not an image to be displayed is a time-series image P2 (step S6), as shown in FIG. 14.

When the determination result in step S6 shows that the image to be displayed is a time-series image P2, the display control section 94 causes the display unit 5 to display a time-series image P2 generated by the image generation section 93 (step S2). The display control section 94 then proceeds to the process in step S7.

On the other hand, when the determination result in step S6 shows that the image to be displayed is not a time-series image P2 (is summed image P1), the display control section 94 causes the display unit 5 to display a summed image P1 generated by the image generation section 93 (step S3). The display control section 94 then proceeds to the process in step S7.

In step S7, the display control section 94 determines whether or not the user has operated the operation unit 3 to switch the displayed image to the other (step S7).

When the determination result in step S7 shows that the switching operation has been performed, the display control section 94 returns to the process in step S6.

When the determination result in step S7 shows that the switching operation has not been performed, the display control section 94 determines whether or not the user has performed operation of stopping displaying the biological state image (step S5).

When the determination result in step S5 shows that the operation described above has not been performed, the display control section 94 proceeds to the process in step S7.

When the determination result in step S5 shows that the operation described above has been performed, the display control section 94 stops displaying the biological state image and terminates the display control process.

The image display apparatus 1A according to the present embodiment described above provides not only the same advantageous effects as those provided by the image display apparatus 1 described above but also the following advantageous effects:

The image display apparatus 1A, which includes the pulse wave detection unit 8, can acquire biological information as appropriate in a position where the image display apparatus 1A is worn. Since the information acquisition section 92 can then process the biological information to acquire the predominance levels and the activity magnitude described above, a biological state image according to biological information detected at desired timing can be displayed.

[Variations of Embodiments]

The invention is not limited to the embodiments described above, and variations, improvements, and other modifications thereof made to the extent that the advantage of the invention is achieved fall within the scope of the invention.

In the first embodiment described above, the external apparatus ED transmits the predominance levels and the activity magnitude described above determined based on detected biological information to the image display apparatus 1, but the invention is not necessarily configured this way. That is, the external apparatus may transmit detected biological information to the image display apparatus, and the image display apparatus may acquire the predominance levels and the activity magnitude described above based on the received biological information and generate and display a biological state image according to the acquired predominance levels and the activity magnitude. That is, the image display apparatus 1 may have the function of the information acquisition section 92.

In each of the embodiments described above, a figure F set in a summed image P1, NA and a time-series image P2 is a circular figure, but the invention is not necessarily configured this way. That is, a figure F may have a rectangular shape or any other shape.

Further, the shape of a figure F according to the predominance levels and the activity magnitude based on the latest biological information may be differentiated from the shape of other figures F, and the color and displayed state of the latest figure F may be changed. For example, the latest figure F may be so displayed that it blinks.

In each of the embodiments described above, a figure F has preset transmittance, and a portion where a plurality of figures F overlap with each other shows a deep color, whereas a portion where the figures do not overlap with each other shows a light color, but the invention is not necessarily configured this way. For example, a figure F based on the latest biological information may be displayed in a predetermined color, and other figures F may be displayed in a color different from the predetermined color. Further, the number of figures set for each predominance level (the number of acquired pieces of biological information) may instead be displayed in the form of a numeral.

Moreover, figures may be arranged with spaces therebetween so that they do not overlap with each other. In this case, the number of figures set for each predominance level may be displayed by using the color of the figure and the density of the color.

In each of the embodiments described above, the color of a figure F set when the sympathetic nerves are dominant is a warm color, whereas the color of a figure F set when the parasympathetic nerves are dominant is a cold color, but the invention is not necessarily configured this way. That is, the color of a figure may be a color other than warm or cold colors and may not even be adjusted for each predominance level. Further, instead of adjusting the color in accordance with the predominance level, the grayscale of a figure F may be increased or decreased in accordance with an increase in the difference in time between the time at which the biological information corresponding to the predominance level is acquired and the current time or the color may be adjusted in accordance with the difference in time.

In each of the embodiments described above, the images P1, P1A, and P2 can be scrolled, and the images P1, P1A, and P2 are switched to one of them and displayed in response to operation performed on the operation unit 3. When a time-series image P2 is scrolled so that the contents thereof based on past biological information are displayed, and the displayed time-series image P2 is then switched to a summed image P1, the summed image P1 to be displayed may be generated based on biological information within a predetermined period from the current time to the time at which the past biological information is acquired. Similarly, when a summed image P1A is displayed and the time-series area TA is scrolled, a graph G according to the position of the scrolled time-series image may be generated, and the graph G may be set in the graph area GA.

In each of the embodiments described above, the predominance level of each of the sympathetic nerves and the parasympathetic nerves is expressed in the form of a numeral ranging from 1 to 10 (including decimal places), and the activity magnitude of the autonomic nerves is expressed in the form of a stepwise numeral ranging from 1 to 4, but the invention is not necessarily configured this way. That is, the numerals according to which the predominance levels and the activity magnitude are evaluated may be changed as appropriate.

Further, the period over which biological information referred to when summed images P1 and NA and a time-series image P2 are generated is acquired and the cycle at which the predominance levels and the activity magnitude described above are acquired can also be changed as appropriate, as described above.

In each of the embodiments described above, the imaging display apparatus 1 and 1A acquire the predominance levels of the sympathetic nerves and the parasympathetic nerves and the activity magnitude of the autonomic nerves based on biological information to generate and display a biological state image (images P1, NA, and P2) based on the predominance levels and the activity magnitude, but the invention is not necessarily configured this way. For example, a PC (personal computer) or any other image generation apparatus may generate and transmit a biological state image, and an image display apparatus may receive and display the biological state image. The invention is applicable also to such an image generation apparatus.

In each of the embodiments described above, a pulse wave is acquired as the biological information, but the invention is not necessarily configured this way. That is, the biological state image described above may be generated and displayed based on any other piece of biological information (cardiogram, body temperature, and blood pressure, for example).

In each of the embodiments described above, the level axis A1 as the first axis and the temporal axis A2 as the second axis are perpendicular to each other, and the level axis A1 and the summation axis A3 are perpendicular to each other, but the invention is not necessarily configured this way. The axes may intersect each other at an angle different from 90. The axes may even be so separated from each other that they do not intersect each other. In addition, the layout of the summed images P1, P1A and the time-series image P2 may be changed as appropriate.

The invention claimed is:

1. An image display apparatus that displays a biological state image showing the state of autonomic nerves based on detected biological information, the apparatus comprising:
a display section that displays an image;
an information acquisition section that acquires predominance level of sympathetic nerve and parasympathetic nerve and an activity magnitude of the autonomic nerve based on the biological information;
an image generation section that generates the biological state image in which a figure having a size according to the acquired activity magnitude of the autonomic nerves is set along a first axis, along one side of which the predominance level of the sympathetic nerve is set with respect to a reference point and along the other side of which the predominance level of the parasympathetic nerve is set with respect to the reference point, in a position according to the acquired predominance levels of the sympathetic nerve and the parasympathetic nerve, wherein in the biological state image generated by the image generation section, the figure is set along the first axis whenever the predominance level of the sympathetic nerve and the parasympathetic nerve and the activity magnitude of the autonomic nerve are acquired, and a portion where the figure overlaps with another figure has a color deeper than the color of a portion where the figures do not overlap with each other; and
a display control section that causes the display section to display the generated biological state image.

2. The image display apparatus according to claim 1, wherein in the biological state image generated by the image generation section, whenever the predominance level of the sympathetic nerve and the parasympathetic nerve and the activity magnitude of the autonomic nerve are acquired, the figure having a size according to the acquired activity magnitude is set not only along the first axis and in a position according to the acquired predominance level of the sympathetic nerve and the parasympathetic nerve but also along a second axis which intersects the first axis and along which time is set and in a position according to the time at which the predominance levels and the activity magnitude are acquired.

3. The image display apparatus according to claim 1,
wherein the image generation section generates the following images as the biological state image whenever the predominance level of the sympathetic nerve and the parasympathetic nerve and the activity magnitude of the autonomic nerve are acquired:
a first image in which the figure is set along the first axis and a portion where the figure overlaps with another figure has a color deeper than the color of a portion where the figures do not overlap with each other; and
a second image in which the figure having a size according to the acquired activity magnitude is set not only along the first axis and in a position according to the acquired predominance level of the sympathetic nerve and the parasympathetic nerve but also along a second axis which intersects the first axis and along which time is set and in a position according to the time at which the predominance level and the activity magnitude are acquired; and
the display control section switches an image to be displayed in the display section between the first image and the second image generated by the image generation section in response to operation performed on the image display apparatus.

4. A display control method for displaying a biological state image showing the state of autonomic nerve based on detected biological information, the method comprising:
acquiring, by a computer, predominance level of sympathetic nerve and parasympathetic nerves and an activity magnitude of the autonomic nerve based on the biological information; and
displaying, by the computer, the biological state image in which a figure having a size according to the acquired activity magnitude of the autonomic nerve along a first axis, along one side of which the predominance level of the sympathetic nerve is set with respect to a reference point and along the other side of which the predominance level of the parasympathetic nerve is set with respect to the reference point, in a position according to the acquired predominance level of the sympathetic nerve and the parasympathetic nerve, wherein in the biological state image, the figure is set along the first axis whenever the predominance level of the sympathetic nerve and the parasympathetic nerve and the activity magnitude of the autonomic nerve are acquired, and a portion where the figure overlaps with another figure has a color deeper than the color of a portion where the figures do not overlap with each other.

5. A non-transitory display control program executed by an image display apparatus that displays a biological state image showing the state of autonomic nerve based on detected biological information and causing the image display apparatus to display the biological state image, the program causing the image display apparatus:

to acquire predominance level of sympathetic nerve and parasympathetic nerve and an activity magnitude of the autonomic nerve based on the biological information; and to display the biological state image in which a figure having a size according to the acquired activity magnitude of the autonomic nerve along a first axis, along one side of which the predominance level of the sympathetic nerve is set with respect to a reference point and along the other side of which the predominance level of the parasympathetic nerve is set with respect to the reference point, in a position according to the acquired predominance level of the sympathetic nerve and the parasympathetic nerve, wherein in the biological state image, the figure is set along the first axis whenever the predominance level of the sympathetic nerve and the parasympathetic nerve and the activity magnitude of the autonomic nerve are acquired, and a portion where the figure overlaps with another figure has a color deeper than the color of a portion where the figures do not overlap with each other.

* * * * *